(12) United States Patent
Gulati (10) Patent No.: US 7,239,974 B2
(45) Date of Patent: Jul. 3, 2007

(54) EXPLOSIVE DEVICE DETECTION BASED ON DIFFERENTIAL EMISSIVITY

(75) Inventor: Sandeep Gulati, La Canada, CA (US)

(73) Assignee: VIASPACE Security Inc., Pasadena, CA (US)

( * ) Notice: Subject to any disclaimer, the term of this patent is extended or adjusted under 35 U.S.C. 154(b) by 0 days.

(21) Appl. No.: 11/350,683

(22) Filed: Feb. 8, 2006

(65) Prior Publication Data

US 2007/0118324 A1 May 24, 2007

Related U.S. Application Data

(60) Provisional application No. 60/739,055, filed on Nov. 21, 2005.

(51) Int. Cl.
*G01K 13/00* (2006.01)
*G06F 15/00* (2006.01)

(52) U.S. Cl. .......................... 702/131; 73/76; 374/121; 429/34; 702/134

(58) Field of Classification Search ................ 702/130, 702/134, 40, 49, 89, 99; 374/1, 29, 121, 374/126, 128; 429/34; 250/227.11, 340; 340/870.17; 73/76
See application file for complete search history.

(56) References Cited

U.S. PATENT DOCUMENTS

| | | | | |
|---|---|---|---|---|
| 4,988,211 A | * | 1/1991 | Barnes et al. ................ | 374/121 |
| 5,021,980 A | * | 6/1991 | Poenisch et al. ............. | 702/134 |
| 5,983,711 A | * | 11/1999 | Pappas et al. ................. | 73/76 |
| 6,963,816 B1 | * | 11/2005 | Poulsen ...................... | 702/134 |
| 7,010,455 B2 | * | 3/2006 | Pieragostini ................. | 702/134 |
| 2006/0127729 A1 | * | 6/2006 | Roscoe et al. ................ | 429/34 |

OTHER PUBLICATIONS

Fuse et al., JP402187691A, Human body detector, Abstract, PUBDate Jul. 23, 1990.*
Lee et al., "Feasibility study on acquisition, tracking, and pointing using earth thermal images for deep-space Ka-band and optical communication", IPN Progress Report 42-155, Nov. 15, 2003.*

* cited by examiner

*Primary Examiner*—John Barlow
*Assistant Examiner*—John Le
(74) *Attorney, Agent, or Firm*—Mintz, Levin, Cohn, Ferris, Glovsky & Popeo, P.C.

(57) ABSTRACT

Techniques for monitoring thermal emissivity levels of human traffic within a plurality of sections of a zone of interest are presented. The thermal emissivity levels are monitored using an infrared detector with sensitivity range of less than fifty milliKelvin, and in some variations, about fifteen to thirty milliKelvin, such as a quantum well infrared photodetector (QWIP) equipped camera. Based on differential emissivity calculations, a determination is made whether the monitored emissivity level corresponds to at least one calibrated emissivity level associated with an explosive material. The monitored emissivity levels are calibrated to eliminate the effects of other synthetic objects such as clothing, personal items, and other harmless objects. The monitored emissivity levels are also buffered against changes in environmental factors.

42 Claims, 4 Drawing Sheets

EXPLOSIVE DEVICE DETECTION BASED ON DIFFERENTIAL EMISSIVITY

This application claims benefit of application Ser. No. 60/739,055 filed Nov. 21, 2005.

BACKGROUND

The present disclosure relates to real-time imaging systems for detecting differential levels of emissivity. In particular, the disclosure relates to detecting explosive devices. The present application claims benefit under 35 U.S.C. 120 of Provisional Application. No. 60/739,055, filed on Nov. 21, 2005 the contents of which are hereby fully incorporated by reference.

Safety is an important consideration, especially at locations where the volume of human traffic is high. At airports, subway entrances, border crossing, sporting events, concerts, and other public gatherings, an intentional detonation of a concealed explosive device may result in numerous human injuries. In such environments, it is difficult to detect a person carrying a concealed explosive device. In addition, it is desirable to identify the person carrying the concealed explosive device at a safe distance from a crowd of people in order to have enough time to react once the detection is confirmed. Past efforts for standoff explosive detection have relied upon X-ray, millimeter wave radar, mass spectrometry and neutron spectrometry. However, these methods have been successful only when in close proximity with the human subject (distances<5 m).

SUMMARY

The methods and apparatus described herein implement techniques for detecting concealed objects based on differential emissivity levels. In one aspect, the methods and apparatus described herein implement techniques for creating a virtual portal representing a zone of interest and monitoring the emissivity levels of human traffic within the zone of interest. The techniques can be implemented to determine if the monitored emissivity level corresponds to at least one calibrated emissivity level associated with a concealed explosive material.

In another aspect, the techniques can be implemented to create a virtual portal representing a zone of interest and to monitor thermal emissivity levels of human traffic within a plurality of sections of the zone of interest. The monitored thermal emissivity can be processed to determine whether the monitored thermal emissivity levels correspond to at least one calibrated thermal emissivity level associated with a synthetic material concealed on a human body.

In another aspect the techniques can be implemented to include a quantum well infrared photodetector having sensitivity range of about fifteen to thirty milliKelvin to monitor thermal emissivity levels of human traffic within a plurality of sections of a zone of interest. A processor can be coupled to the quantum well infrared photodetector and determine whether the monitored thermal emissivity levels correspond to at least one calibrated thermal emissivity level associated with a concealed explosive material on a human body by performing differential emissivity calculation and black body algebra. The processor can also track the detected concealed explosive material as the human body moves through the zone of interest. In addition, a data repository can be coupled to the processor to store data associated with calibrated thermal emissivity levels for factors selected from a group including ambient background, an exterior surface of a human, clothing, personal articles, computing devices, and an explosive material.

In some implementations, the following features can be included. A human associated with each thermal emissivity level corresponding to the concealed explosive material can be identified. The identified human can also be tracked by comparing the detected emissivity level against multiple pre-determined empirical models. The monitored thermal emissivity levels can also be calibrated to distinguish between the concealed explosive material and a non-explosive material including a cell phone, a pager, a key chain, and other non-explosive synthetic objects based on differential emissivity measured between different synthetic objects. The monitored thermal emissivity levels can also be calibrated to identify a differential emissivity between a clothing material including fabric, leather, synthetic polymer, and other clothing material and the concealed explosive material. In addition, the zone of interest can extend from three feet to five kilometers. Further, monitoring the emissivity levels to identify the concealed explosive material can include identifying temperature differences within a range of about five milliKelvin and fifty milliKelvin. The emissivity levels can be monitored using a long wave infrared detector such as a quantum well infrared photodetector. The plurality of sections of the zone of interest can correspond to pixels of the quantum well infrared photodetector.

In some implementations, the following features can be included singly or in combination (depending on the desired configuration). The techniques may be implemented to determine if the monitored thermal emissivity level for a section of the zone of interest is associated with a calibrated thermal emissivity level for a factor selected from a group including ambient background, an exterior surface of a human, a clothing material, a personal article, a computing device, and/or an explosive material. The thermal emissivity levels can be monitored from a fixed distance and empirically associated with one or more factors selected from a group including ambient background, an exterior surface of a human, clothing material, a personal article, a computing device, and/or an explosive material. In some variations, successive quantum well infrared photodetector image frame can be processed to confirm detection of the concealed explosive material, identify a specific human carrying the concealed explosive material, and/or identify a specific location of the concealed explosive material with a margin of error less than a fraction of an inch. The techniques can be implemented to detect plastic explosive materials, timing mechanisms, wiring devices, explosive trigger mechanisms, dud explosives, and wired devices.

In some implementations, the following features can be included. A facial expression and sweat on a human target can be detected to facilitate the detection of the concealed explosive material. Monitored thermal emissivity levels corresponding to at least one calibrated thermal emissivity level associated with the concealed explosive material can be based on a differential emissivity, wherein the differential emissivity is buffered against changes in the ambient background including temperature, wind condition, humidity, hail, and/or snow. Pixels of a quantum well infrared photodetector array can be repeatedly scanned to detect a change in emissivity to detect a concealed object. A texture in an estimated emissivity map can be processed to identify a type of explosive material detected and increase accuracy of detection. Also, a morphology of an estimated emissivity map can be processed to identify a type of explosive material detected, and a contour of the estimated emissivity map can be processed to further increase accuracy of detection.

The techniques can be implemented to detect explosive material concealed on a human suicide bomber. In addition, the thermal emissivity levels of human traffic can be monitored at airports, border crossings, entrance to subways and other transportation facilities and sensitive facilities, and public functions and sporting events.

In some implementations, one or more of the following features can also be included singly or in combination. Data associated with calibrated thermal emissivity levels for factors selected from a group including ambient background, an exterior surface of a human, clothing, personal articles, computing devices, and/or an explosive material can be stored in a data repository. The calibrated thermal emissivity levels can be determined by empirically associating the factors at a distance corresponding to a length between the radiation detection unit and the zone of interest. The emissivity levels can be monitored by a radiation detection unit having an optical element with a focal length corresponding to the zone of interest. In addition, a video camera can be positioned to monitor the zone of interest and display video images captured from the video camera on a video display device.

A secondary detection system can alternatively implemented to confirm detection of the concealed explosive material. The radiation detection unit can be portable including a portable camera, a wireless device, and a hand-held device. Alternatively, the radiation detection unit can be a fixed device mounted on a building or a vehicle. The radiation detection unit can be a quantum well infrared photodetector sensor disguised as a regular CCD camera. The emissivity levels monitored from a fixed distance are robust and thus buffered against variations in human gait or movement to allow easy tracking of a person carrying the concealed explosive material as the person moves through the zone of interest. The emissivity levels are not affected by variations in environmental factors such as temperature.

The techniques described herein can be implemented to realize one or more of the following advantages. For example, the real-time explosive device detection system can be implemented to detect a concealed explosive material in a high traffic zone of interest. Alternatively, the emissivity levels of human traffic can be monitored in enterprise, departmental and retail facilities to prevent theft by detecting stolen goods concealed on a person. Further, the emissivity levels of human traffic can be monitored to prevent theft and removal of proprietary material on portable storage media including memory stick, portable hard drive, removable storage media, and CD.

These general and specific aspects can be implemented using an apparatus, a method, a system, or any combination of an apparatus, methods, and systems. The details of one or more implementations are set forth in the accompanying drawings and the description below. Further features, aspects, and advantages will become apparent from the description, the drawings, and the claims.

BRIEF DESCRIPTION OF DRAWINGS

Like reference symbols in the various drawings indicate like elements.

DETAILED DESCRIPTION

The following describes techniques for detecting object of interest such as explosive material concealed on a human body based on a differential emissivity between the explosive material and non-explosive materials including the human body, an ambient background, a synthetic personal object (such as a cell phone, car keys, etc.), and/or clothing. In the following description, for the purpose of explanation, numerous specific details are set forth in order to provide a thorough understanding of the present disclosure. It will be apparent, however, to one of ordinary skill in the art that the present disclosure may be practiced without these specific details. In other instances, well-known structures are shown in block diagram form. Further, although the foregoing descriptions focus on monitoring emissivity levels to identify explosive materials, it will be apparent to one of ordinary skill in the art that the techniques can be implemented to detect any object of interest with different emissivity levels.

Emissivity

A blackbody emits energy with a Planck distribution. A blackbody emitter is useful for comparison with materials that do not emit perfectly at all wavelengths, which is the case for most of the matter in the universe. Molecules that make up different materials (gases, liquids, and solids) are formed from atoms bonding together. The molecules vibrate when agitated, and this agitation arises when light of just the right wavelength hits a particular molecule. Once the molecule starts vibrating, the molecule re-radiates the same wavelength of light. This is the process of absorption and emission. The wavelengths of light that cause the molecules to vibrate occur in the infrared region. Every unique molecule has its own characteristic frequency of vibration. So, unlike a blackbody emitter, molecules emit energy that departs from a Planck distribution. Thus, infrared energy emitted by the vibrating molecules can be used to identify the molecules.

One of the ways to describe the infrared energy emitted by molecules is in terms of radiance: watts of energy per unit of area. With changes in temperature, come changes in radiance. For example, the radiance from a material at one temperature will be different from that at another temperature. In order to make comparisons of emission from materials at different temperatures, the temperature effect needs to be removed. This removal is accomplished mathematically by dividing the radiance spectrum of a selective emitter by that of a blackbody (perfect emitter) at the same temperature. The result is called an emissivity spectrum. Because emissivity results from dividing one radiance spectrum by another, the units of watts/area cancel. Emissivity then, is a fractional representation of the amount of energy from some material vs. the energy that would come from a blackbody at the same temperature. The places in an emissivity spectrum that have a value less than one are the wavelength regions that molecules are absorbing energy.

Most surfaces are not blackbody emitters, and emit some fraction of the amount of thermal radiation as component of a blackbody. This fraction is known as emissivity. If a surface emits ½ or 0.5 as much radiation at a given wavelength and temperature as a blackbody, it is said to have an emissivity of 0.5. If it emits $\frac{1}{10}$ or 0.1 as much as a blackbody, it has an emissivity of 0.1 and so on. A blackbody has an emissivity of 1.0 at all temperatures and wavelengths.

A sensor with high resolution of emissivity may be used to process real-time differential emissivity levels. Ideally, the sensor should have substantially a $10^{-6}$ resolution based on 15-30 milliKelvin. For example, a quantum well infrared photodetector (QWIP) sensor (available from QWIP Technologies, Inc.) may be used. Thermal imaging systems with sensitivity less than 50 milliKelvin can be ineffective when performing detections at standoff distances of interest (>10 meters) or for detecting explosives camouflaged below thick clothing.

A fast acting sensor (e.g., a QWIP sensor), with interpretation time<10 millisecond is implemented to create a real-time improved explosive device (IED) detector for imaging and isolating a target subject in a crowd.

Real-Time Improved Explosive Device Detection System

Figure 1A:
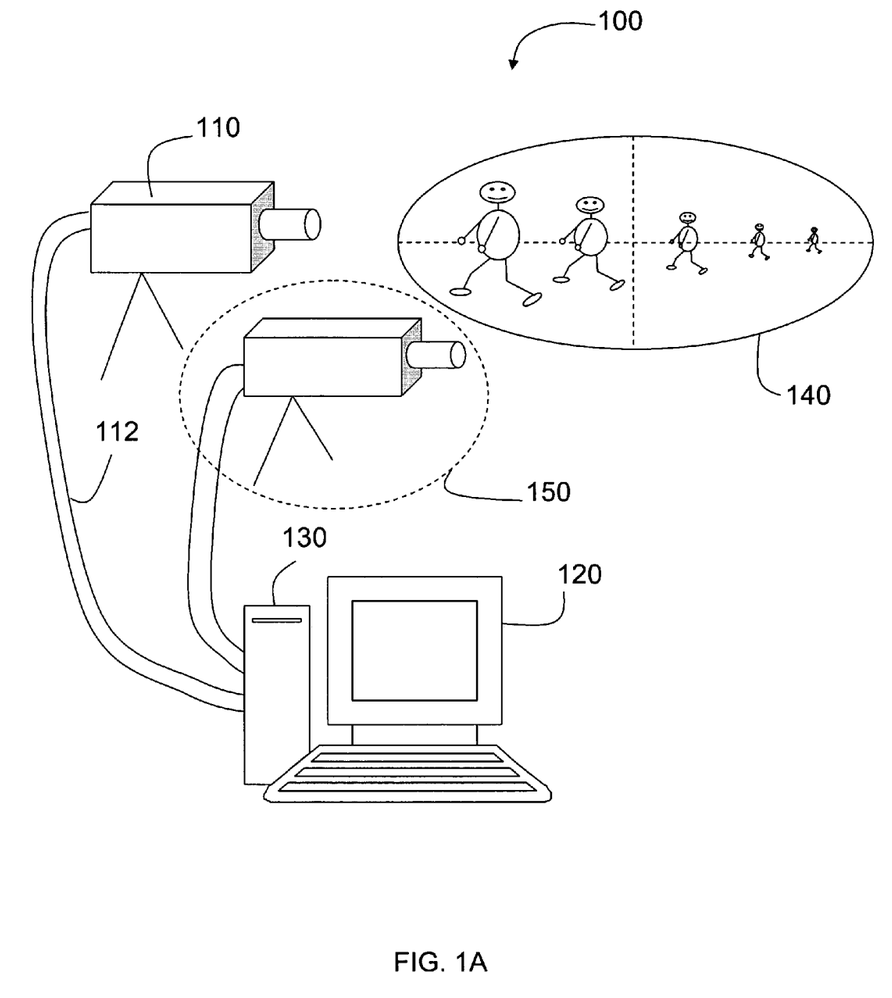
FIGS. 1A-1B are block diagrams of a real-time explosive device detection system.
Figure 1B:
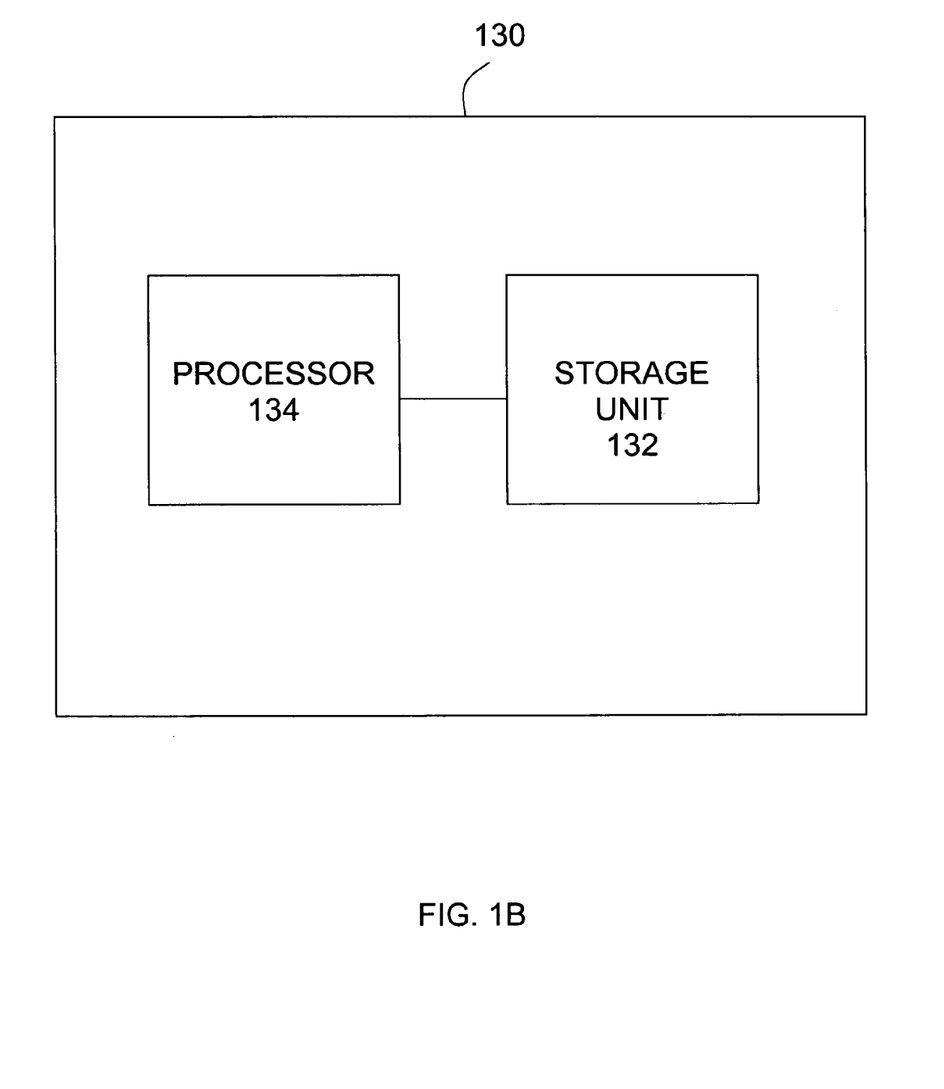

FIGS. 1A-1B are block diagrams describing an improved explosive device detection (IED) system 100. The IED system 100 can include a radiation detection unit 110, an IED processing unit 130, and a display unit 120. The IED processing unit 130 can also include at least a storage unit 132 for storing computer executable instructions to be processed by a processor 134. The storage unit 132 can also include storage repositories such as database for storing various data. The system 100 can also include a secondary detection system 150 coupled to the processing unit 130 and configured to confirm detection of the concealed explosive material. The secondary detection unit 150 can be implemented to include either X-ray imaging system, a millimeter wave radar, and/or a laser ranging device for performing a high resolution scan or neutron spectral analyzer. The secondary detection system 150 may not include a radiation detector with high sensitivity such as the QWIP camera included in the IED system 100. By implementing alternative detection components with less sensitivity, the secondary detection system 150 provides additional simple information to complement the data obtained from the IED system 100.

The radiation detection unit 110 can be configured to monitor thermal emissivity levels of human traffic within a zone of interest 140. The zone of interest 140 may include multiple sections and can extend various distances. For example, the zone of interest can extend from about three feet to about five kilometers. The radiation detection unit 100 can be coupled to the IED processing unit 130 through a communication link 112. The communication link 112 can be a bi-directional communication link between the radiation detection unit 110 and the IED processing unit 130. In some implementations, the communication link 112 is a physical cable or wire link compatible with typical data communication standards including IEEE 1394 (FireWire) connection, Universal Serial Bus (USB) connection, or other serial or parallel data connections. In other implementations, the communication link 112 is a physical cable or wire link compatible with typical digital video communication standards including high-definition multimedia interface (HDMI), digital visual interface (DVI), S-Video, composite video, component video, and other suitable video data connections. In yet other implementations, the communication link 112 may be a wireless communication link (e.g., Bluetooth, infrared, or other wireless communication).

The radiation detection unit 110 can be implemented as a long wave infrared detector. One example of a long wave infrared detector may be an infrared camera configured with a highly sensitive array of infrared photodetectors known as quantum-well infrared photodetectors (QWIPs). Advances in the growth of gallium arsenide semiconductors have led to QWIPs sensitive to long-wavelength infrared radiation. A camera equipped with a QWIP sensor has a sensitivity to distinguish temperature differences of fifty milliKelvin or less. The radiation detection unit 110 may include an optical element having a focal length corresponding to the zone of interest to facilitate monitoring emissivity levels of human traffic at a fixed distance. In some implementations, the radiation detection unit 110 may be a portable device including a portable camera, a wireless device, and a hand-held device. In other implementations, the radiation detection unit 110 may be a fixed device mounted on a building, or a vehicle. In yet other implementations, the radiation detection unit 110 may be a QWIP sensor camera disguised as a regular CCD camera.

Figure 2:
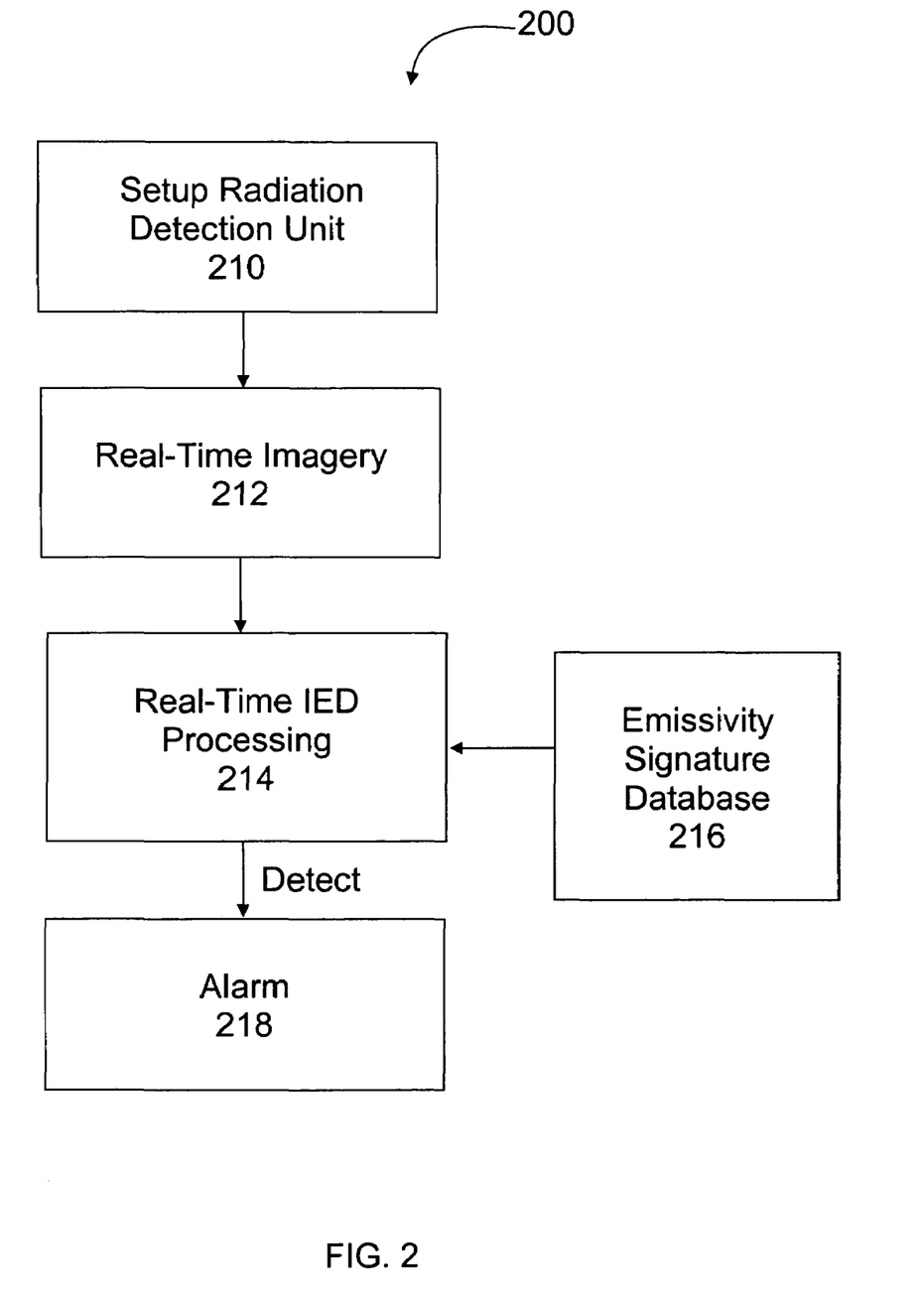
FIG. 2 is a flow chart of a process of monitoring emissivity levels of human traffic within a zone of interest to determine a presence of concealed explosive material.

The radiation detection unit 110 is used to monitor human traffic by capturing real-time images and sending the images to the IED processing unit 130 to determine whether the monitored thermal emissivity levels correspond to at least one calibrated thermal emissivity level associated with a concealed synthetic object including an explosive material, a weapon, and stolen goods. FIG. 2 is a flow chart describing a process of detecting an explosive material concealed on a human body based on differential emissivity between the explosive material and non-explosive materials including the human body, an ambient background, a synthetic personal object (e.g., a cell phone, car keys, and other synthetic objects with a know emissivity level), and clothing. The radiation detection unit 110 is configured at 210 to monitor human traffic within a zone of interest 140. The zone of interest 140 may be divided into multiple segments. The radiation detection unit 110 may be a QWIP sensor camera calibrated to monitor emissivity levels of human traffic within a zone of interest 140 at a fixed distance. Real-time thermal radiation images of human traffic within the zone of interest 140 at the fixed distance are captured at 212 by the radiation detection unit 110. The captured real-time images are processed by the IED processing unit 130 to detect target objects concealed on a human body.

Typically, a bomb detection system is implemented using a real physical scanning and detection portal, where a target human must walk through the portal. For example, an metal detector is a portal physically stationed at a set location for having people walk through the metal detector. This may not be effective for many reasons. For example, a potential target human carrying a concealed explosive material has the option of not walking through the detector. Also, the metal detector is a close proximity detector in that the detector is in close proximity of human casualty. Further, this physical portal cannot be used to track the target human carrying concealed explosive material.

According to one aspect, the drawbacks of requiring a physical detection portal and close proximity to the subject are eliminated. The IED system 100 allows creation of a arbitrary virtual portal in any free space that is setup as a monitoring focal point at various distances from the detection system, IED system 100 (e.g., 50 feet away, 200 feet away, etc.). The created virtual portal determines the area represented by the zone of interest 140. As the target of interest moves closer to the detection system, the detected emissivity, as a function of distance from blackbody (human carrying an explosive) is compared against models stored in a calibrated database. The detection system uploads different models and performs model switching as the target moves.

Each model in the calibrated database is at least based on a specific distance. For example, the detection system may initially create a virtual portal in free space 500 meters away from the detection system. Thus the detection system detects the emissivity level of a human target initially at a distance of 500 meters. As the human target moves either closer or further away from the initial detection point, the detection system compares the measured emissivity in real time against a set of calibrated data models stored in the calibrated database corresponding to a specific distance. If the human target is moving closer to the detection system, the detected emissivity of the moving human target is compared against calibrated models set for each decremental distances (e.g., 500 meters, 490 meters, 480 meters, and so forth) until a match is detected and confirmed or it is concluded that human target is not carrying a concealed IED. If the human target is moving away from the detection system, the system compares the detected emissivity against calibrated models set for each incremental distance. If the first model does not provide a match, a different model set for the next distance is uploaded. By switching through a set of models corresponding to different distances, the detection system eliminates the need to keep track of or measure the distance between the target of interest and the detection system. Further, by comparing against stored calibrated data models, target tracking is accomplished without any additional processing as long as the target of interest is within the field of view. The rate of model switching is based on a pre-calibrated and stored estimate of human gait. For example a typical walking subject would exhibit speeds of 0.5 mph to 5 mph.

In one implementation, the radiation detection unit 110 is configured to monitor human traffic at a fixed distance far enough to reduce each person down to a few pixels in the captured image. Each pixel represents emissivity level of all black bodies at that location. For example, when a person is concealing an explosive material under multiple layers of clothing, the pixel represents the combined emissivity level of a combined black body, which is a combination of a natural black body (e.g. human body) and man made or synthetic black body (e.g., clothing). The clothing material acts as an interfering black body. In one aspect of the techniques, a pixel of interest is selected and processed at 212 by performing differential emissivity calculation. The pixel of interest must have a different emissivity level when compared to neighboring pixels to infer presence of a different non-linear combination of black bodies represented by the pixel of interest in comparison to neighboring pixels. This differential emissivity calculation is a practical advantage of monitoring emissivity levels of human traffic at the fixed distance where each person is reduced down to a few pixels. Since each pixel at such distance represent a higher surface area, the differential emissivity levels between neighboring pixels can be exploited to quickly identify presence of different combinations of black bodies.

One pixel at a time (or an aggregation of multiple pixels), the emissivity levels at the fixed distance are empirically associated with one or more factors selected from a group comprising ambient background, an exterior surface of a human, clothing, personal articles, computing devices, and an explosive. In some implementations, pixels of a QWIP array may be scanned repeatedly to detect a change in emissivity corresponding to a concealed object. The emissivity levels can be calibrated by empirically measuring the emissivity levels of a known object and a combination of known objects. For example, people wearing different combinations of known clothing and concealing synthetic objects including explosive devices are monitored as they walk through the zone of interest 140. The monitored emissivity levels are stored in a storage location such as an emissivity signature database at 216. These known signatures of emissivity levels can be used to facilitate real-time detection of concealed devices including explosive materials.

In some implementations, as the target of interest moves within the created virtual portal, the detection system performs pixel by pixel scan processing. As stated above, the detection system creates a virtual portal in any free space to monitor emissivity levels of human traffic. Initially, the virtual portal is created at an arbitrary distance far away from the detection system. For example, the initial detection range may be set for 500 meters away from the detection system. When a target of interest is a human carrying a concealed explosive, the concealed explosive material at the initial 500 meter distance may be represented by a single pixel in a captured image. As the human target moves closer to the detection system, the explosive material will be represented by more and more pixels. At 400 meters, three pixels may represent the explosive material, for example. Conversely, if the person moves further away from the detection system, the explosive material will be represented by lesser and lesser pixels. This pixel by pixel scan processing allows the detection system to monitor and tract the target of interest both as the target moves closer and further away from the virtual portal.

In addition, this pixel by pixel scanning strategy is a control system that allows the detection of a single pixel and using the pixel information to back infer to the source, such as the human body. Therefore, the pixel by pixel scanning strategy eliminates the need to identify the human target first and allows monitoring and tracking of emissivity levels to be performed in real time and at a considerable distance away from the detection system. Being able to detect explosive material concealed on a human body far away from the detection system provides more time to prevent detonation of the explosive material. If detection of the target human was required before making a positive detection of the explosive material, there may be no time left to safely deal with the explosive material and avoid harm.

In developing an empirical knowledge base for emissivity signatures, a test matrix with at least six variable attributes are implemented. The attributes can include the following:
1. standoff distance from scanning portal;
2. clothing materials (e.g., cotton, polymers, polyester, jute, denim) and types of clothing (e.g., jackets, sweatshirts and sports windbreaker);
3. ambient temperature and wind velocity;
4. objects of interest (e.g., explosives of interest and portable electronic devices such as cell phones, portable radios, mp3 players, and RFID-based key chains);
5. background field of view including road, vehicles, human cluster, buildings, foliage, and glass; and/or
6. human gait.

Series of controlled images can be captured, in duplicate or triplicate, over a test space defined as the cross product of above mentioned attributes. The series of images can be captured using a QWIP camera. The individuals pixels from each captured image are grouped based on a condition represented by the corresponding pixel. For example, all pixels corresponding to a building in the background are grouped together to obtain an emissivity statistic for that background condition. Once the images are deconstructed to form pixel groupings with the homologous attribute, emissivity statistics for a particular condition are calculated.

Emissivity statistics can be represented to include at least the mean, standard deviation, and skewness. Model parameters are then used to develop an emissivity signature database.

The IED processing unit 130 processes each pixel of the captured image at 214 to determine if the monitored emissivity level corresponds to a predetermined differential emissivity level between different materials so that the presence of an explosive material concealed on a human body can be identified. The differential emissivity levels are calibrated against the calibrated emissivity levels of known objects stored in the emissivity signature database at 216. In one implementations, the radiation detection unit 110 is configured to monitor human traffic at a fixed distance far enough to reduce each person down to a few pixels in the captured image. Each pixel represents emissivity level of all black bodies at that pixel location. For example, when a person is concealing an explosive material under multiple layers of clothing, the pixel represents a non-linear combined emissivity level of a combined black body, which is a combination of a natural black body (e.g. human body) and man made or synthetic black body (e.g., clothing). The clothing material acts as an interfering black body. For each pixel, the emissivity levels at the fixed distance are empirically associated with one or more factors selected from a group comprising ambient background, an exterior surface of a human, clothing, personal articles, computing devices, and an explosive material. The differential emissivity between a human body, a background black body, and a camouflaged object acting as a black body of interest can be exploited.

In some implementations, additive black body algebra may be implemented to infer the presence of the camouflaged object on a human body. The camouflaged object is a target object to be detected. When the detection system detects an emissivity level, the detected emissivity level is automatically processed to determine if the emissivity level corresponds to an emissivity level produces by a combination of harmless blackbodies (e.g., a person wearing a sweater and carrying a mobile phone) or an emissivity level produces by a combination of blackbodies that include explosive material (e.g., a person wearing a jacket and concealing explosive material underneath the jacket). This determination is performed by comparing the detected emissivity level against empirically derived and calibrated data models and performing black body algebra. The detected emissivity level is deconstructed to identify the individual constituent black body that produced the detected emissivity when combined together using black body algebra. This determination is perform for each pixel and neighboring pixels are checked using differential emissivity calculations. Since, a target human does not cover his entire body with explosive material, there will be a difference in emissivity levels from one pixel to an adjacent pixel. Therefore the differential emissivity calculation is performed to compare the pixels of one area (e.g., the area representing the explosive material) against pixels of adjacent area (e.g., the area representing human body not covered by the explosive material). Thus, the differential emissivity is calculated over different materials, over time, and over adjacent pixels.

Blackbody algebra incorporates the following concepts. The spectral radiance ($L_\lambda$) of electromagnetic radiation from a blackbody at temperature T is given by Planck's law in Equation 1.

$$L_\lambda = \frac{2hc^2}{\left[\lambda^5\left(e^{\frac{hc}{\lambda kT}} - 1\right)\right]}$$ (Equation 1)

h=Planck's constant (joule per hertz)
c=speed of light (meters per second)
$\lambda$=wavelength (meters)
k=Boltzmann's constant (joules per Kelvin)
T=temperature of the blackbody (Kelvin)
e=base of natural logarithm As a blackbody is Lambertian, emittance is linked to spectral radiance by a normalization factor $\pi$ as shown in Equation 2.

$$M_\lambda = \frac{2\pi hc^2}{\left[\lambda^5\left(e^{\frac{hc}{\lambda kT}} - 1\right)\right]}$$ (Equation 2)

Natural substances on the Earth's surface and the atmosphere are not true blackbodies, and thus emit less energy than forecasted by Planck's law at different wavelengths as compared to synthetic objects. These natural substances are graybodies, absorbing and emitting energy only at certain wavelengths. Emissivity is the ratio between graybody emittance and blackbody emittance at the same temperature, and can be defined spectrally or integrated throughout all wavelengths, in addition, total blackbody emittance (M) is proportional to the fourth power of thermodynamic temperature $T^4$ according to Stephan-Boltzmann law or Stephan's law as defined in Equation 3.

$$M = \sigma \cdot T^4$$ (Equation 3)

$\sigma$=Stephan-Boltzmann constant $$\sigma = 5.67 \times 10^{-6} \frac{W}{m^2 K^4}$$

T=temperature (Kelvin)
W=Watts
m=meter
K=Kelvin

Accordingly total emittance (M) for a natural substance can be defined by Equation 4.

$$M = \epsilon \cdot \sigma \cdot T^4$$ (Equation 4)

$\epsilon$=graybody emissivity

For synthetic blackbodies, (such as camouflaged explosives), linearized radiative heat transfer law is applied as shown in Equation 5.

$$q = \varepsilon \cdot \sigma \cdot A(T_1^4 - T_2^4)$$ (Equation 5)

The synthetic object has "full view" of a blackbody environment at absolute temperature $T_2$. Assume the camouflaged black body is a system enclosure with average surface temperature $T_1$ that is completely surrounded by an ambient temperature $T_2$ (e.g., clothing), $T_1$ and $T_2$ should be of similar magnitude on the absolute temperature scale. Then, emittance for synthetic objects can be solved by applying Equation 6.

$$q = h_r A(T_1 - T_2) \quad \text{(Equation 6)}$$

$h_r$ = radiative "heat transfer coefficient"

This provides a good approximation of radiative "heat transfer coefficient" ($h_r$) quantity as given by Equation 7.

$$h_r = 4\sigma\epsilon T_m^3 \quad \text{(Equation 7)}$$

$T_m$ = arithmetic mean of $T_1$ and $T_2$.

Using these equations, empirical experiments can be implemented to determine the heat transfer coefficient ($h_r$) for different bodies of interest. Based on the determined value of the heat transfer coefficient, ($h_r$) each analyzed pixel in a captured image can be used to back infer the type of material or camouflaged material.

If the pixel value is not within a range of calibrated emissivity level representing the non-linear combination of the human body (natural black body), layers of clothing (synthetic black body), and an explosive material (target synthetic black body), then the IED processor 130 moves on to process the next pixel of interest. If a pixel is identified to have an emissivity value corresponding to a calibrated emissivity level associated with a person concealing an explosive material, the pixel is further processed to identify the type and location of the explosive material, The person concealing the explosive material is also identified and tracked while moving through the zone of interest 140.

When monitoring and tracking a person moving across the zone of interest 140, the emissivity levels stay substantially constant over approximately 100 frames. The IED processing unit 130 may process successive QWIP image frames to confirm detection of the concealed explosive material. When the detection is confirmed, an alarm may, at 210, be activated. In addition, the successive QWIP image frames may be processed to confirmation identification of a specific human carrying the concealed explosive material. The IED processing unit 130 may be able to identify a specific location of the concealed explosive material on the human body with a margin of error less than a fraction of an inch.

Equations (1)-(8) below describes a process of processing successive image frames (e.g., QWIP image frames).

$$\text{Image } I_1 \text{ at time } t_1 \quad (1)$$

$$\text{Image } I_2 \text{ at time } t_2 \quad (2)$$

$$\text{Image } I_3 \text{ at time } t_3 \quad (3)$$

$$\vdots$$

$$\text{Image } I_k \text{ at time } t_k \quad (4)$$

$$\Delta_1 = I_2 - I_1 \quad (5)$$

$$\Delta_2 = I_3 - I_2 \quad (6)$$

$$\Delta_3 = I_3 - I_4 \quad (7)$$

$$\Delta_{k-1} = I_k - I_{k-1} \quad (8)$$

Where $\Delta_{i, j, \ldots}$ are scalable denoting differential emissivities from IED object estimated by image differences. Also, $\Delta_i \to$ converges or $\Delta_i - \Delta_{i-1} \to 0$ as time i, j, k . . . exceeds 5-15 frame grabs.

The above equations are implemented to compute changes in pixel emissivity over time and changes from the model. These equations facilitate calculations that provide a system to automatically detect when the emissivity estimated from a single pixel corresponds to a detection of a concealed explosive. The pixel information allows a determination of whether the emissivity detected originated from a natural object (e.g., human and background) or from an explosive acting as a black body.

With a fast responding camera, $P_{FA} \to 0$ and $P_D \to 1$ as system reaches an adiabatic (or stable) state, where $P_{FA}$ is the probability of false alarm and $P_D$ is the probability of detection. Empirically, integration time >5 millisecond and >10 frames have been found to be necessary to achieve detection.

Based on the differential emissivity calculated, the IED processing unit 130 may be able to detect concealed explosive materials including plastic explosive material, timing mechanisms, explosive trigger mechanisms, and wiring devices. The techniques for calculating the differential emissivity may also be implemented to detect concealed explosive material comprising dud explosives and wired devices. In some implementations, the real-time IED detection system 100 may be implemented to determine whether the monitored thermal emissivity levels correspond to at least one calibrated thermal emissivity level associated with a synthetic material concealed on a human body, wherein the synthetic material comprises a firearm, a portable electronic device, a chemical material, and a stolen good. For example, the real-time IED detection system 100 may be implemented to prevent theft in enterprise, departmental and retail stores, and other facilities where theft of merchandise is a concern. Application—theft and removal of proprietary material on memory stick, media, CD etc.

By effectively calibrating the monitored emissivity levels and taking advantage of the robustness of monitoring at a fixed distance, the calculated differential emissivity is buffered against large changes in the ambient background including temperature, wind conditions, humidity, hail, and snow. Also, when tracking the specific human identified to have a concealed explosive material, the thermal emissivity levels monitored from a fixed distance are buffered against variations in human gait or movement. In some implementations, the real-time IED detection system 100 may be implemented to monitor human traffic at airports, border crossing, entrance to subways and other transportation facilities and sensitive facilities. In other implementations, the real-time IED detection system 100 may be implemented to monitor human traffic at public functions and sporting events.

In some implementations, properties of an estimated emissivity map may be processed to identify a type of explosive material and to increase accuracy of detection. The properties of the estimated emissivity map may include a texture, a morphology, and contour. A pixel-based analysis having multiple pixels represent an object of interest can result in some variation in the estimated intensity from pixel to pixel. This variation can be due to several reasons such as background noise, electronic noise, clutter, and imaging imperfections. However, information obtained by performing statistics of variation in the estimated intensity of adjacent pixels provides valuable insights on the concealed object of interest or the absence of such an object. Texture refers to the variation in adjacent pixel intensities. Grouping of pixels with similar intensities leads to object morphology and contour. Texture, morphology, and contour can be used to increase the confidence of the assessment. For example, a Laplacian filter can reveal low frequency artifacts in the image coming from natural variations due to clothing. High frequency artifacts on the other hand can reveal present of a anomaly corresponding to some concealed object such as cell phone or explosive. Texture analysis can further reveal information to separate a electronic device from explosive based on the edge and curvature properties. Overlaying emissivity contours on segmented human individual contour can provide further evidence for presence of concealed objects In some implementations, the techniques may further be implemented to identify facial expressions and detect the presence of sweat on a human target. On a human body, the emissivity level of the head, is higher than other parts of the body. Therefore, a black body algebra of a single human body may be performed to identify the differential emissivity as the person's head and to immediately recognize that the emissivity reading does not represent an explosive material. For example, a person on a cold day may be wearing a muffler wrapped around his face, and the pixel representing the emissivity level of a combination of his face and the muffler may appear as a concealed object. By recognizing human facial expression in addition to detecting the presence of sweat on the human body may facilitate eliminations of false positive detections of the concealed explosive material.

Figure 3:
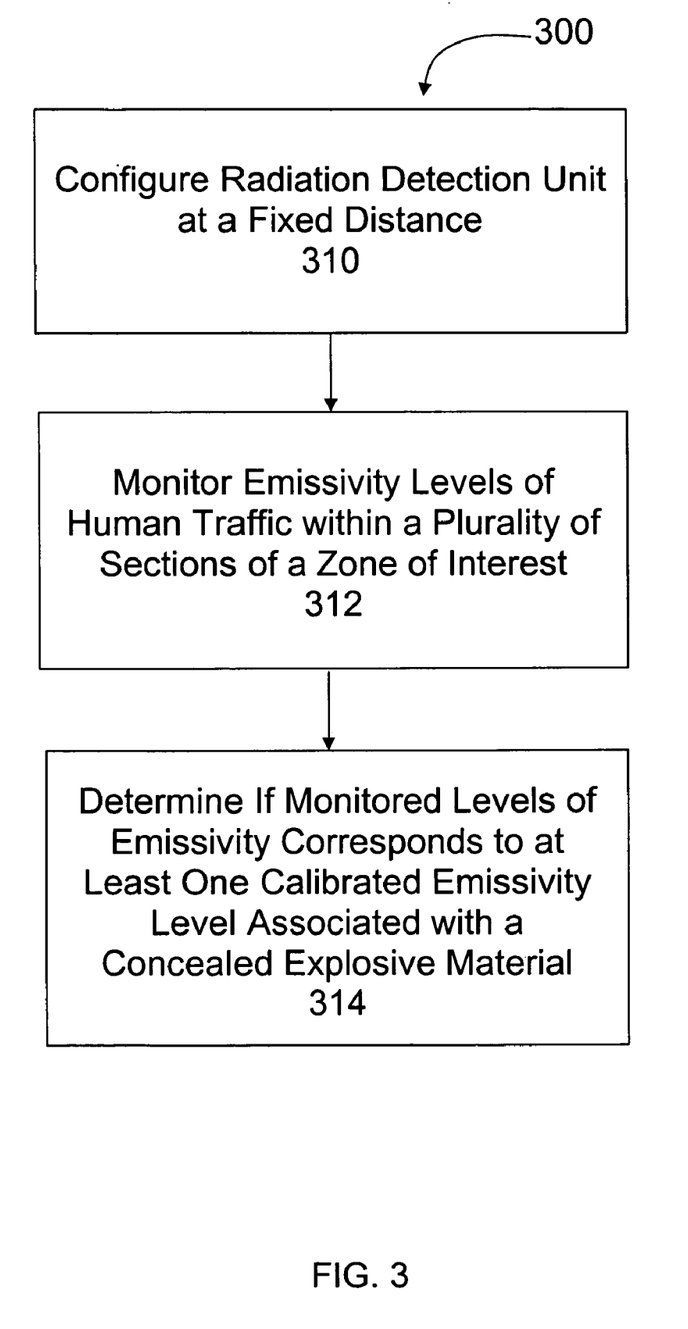
FIG. 3 is a flow chart of a process of implementing the real-time explosive device detection system.

FIG. 3 is a flow chart describing a general process of detecting concealed explosive device. A radiation detection unit is configured to monitor emissivity levels of human traffic within a zone of interest at a fixed distance at 310. The emissivity levels of human traffic are monitored within a plurality of sections of a zone of interest at 312. The monitored emissivity levels are processed to determine if they correspond to at least one calibrated emissivity level associated with a concealed explosive device. In some implementations, the monitored emissivity levels may be implemented to detect stolen goods concealed on a person.

Processors suitable for the execution of the techniques described above include, by way of example, both general and special purpose microprocessors, and any one or more processors of any kind of digital computer, including graphics processors, such as a GPU. Generally, the processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of non volatile memory, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, the systems and techniques described herein can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

A number of implementation of the disclosure has been described. Nevertheless, it will be understood that various modifications may be made without departing from the scope of the disclosure.

What is claimed is:

1. A method comprising:
   creating a virtual portal representing a zone of interest;
   monitoring thermal emissivity levels of human traffic within a plurality of sections of the zone of interest;
   determining whether the monitored thermal emissivity levels correspond to at least one calibrated thermal emissivity level associated with an object of interest by:
      identifying a human associated with thermal emissivity levels corresponding to the object of interest;
      uploading a plurality of pre-determined empirical models to compare the monitored emissivity levels against the models;
      performing model switching to compensate for a change in distance between the human and a emissivity monitoring system as the human carrying the object of interest moves; and
      tracking the identified human within the zone of interest by comparing the detected emissivity level against the plurality of pre-determined empirical models; and
   initiating notification of a user indicating that the object of interest is within the zone of interest.

2. A method as in claim 1, wherein the object of interest is a concealed explosive material.

3. A method as in claim 2, further comprising: calibrating the monitored thermal emissivity levels to distinguish between the concealed explosive material and a non-explosive material including a cell phone, a pager, a key chain, and other non-explosive synthetic objects based on differential emissivity between different synthetic objects.

4. A method as in claim 2, wherein the concealed explosive material includes at least one of a plastic explosive material, a timing mechanism, a wiring device, an explosive trigger mechanism, a dud explosive, and a wired device.

5. A method as in claim 2, further comprising:
   detecting a facial expression and sweat on a human target to facilitate the detection of the concealed explosive material.

6. A method as in claim 2, further comprising processing a texture in an estimated emissivity map to identify a type of explosive material detected and increase accuracy of detection.

7. A method as in claim 6, further comprising processing a morphology of an estimated emissivity map to identify a type of explosive material detected; and processing a contour of the estimated emissivity map to further increase accuracy of detection.

8. A method as in claim 2, wherein the explosive material is concealed on a human suicide bomber.

9. A method as in claim 1, further comprising: calibrating the monitored thermal emissivity levels to identify a differential emissivity between a clothing material including fabric, leather, synthetic polymer, and the object of interest hidden under the clothing material.

10. A method as in claim 1, wherein the zone of interest extends from three feet to five kilometers.

11. A method as in claim 1, wherein the monitoring is operable to identify temperature differences within a range of about five milliKelvin to fifty milliKelvin to identify the concealed explosive material.

12. A method as in claim 1, wherein the monitoring utilizes a long wave infrared detector.

13. A method as in claim 1, wherein the infrared detector is a quantum well infrared photodetector QWIP.

14. A method as in claim 13, further comprising repeatedly scanning pixels of a infrared photodetector array to detect a change in emissivity to detect a concealed object.

15. A method as in claim 1, wherein the plurality of sections of the zone of interest correspond to pixels of an infrared photodetector.

16. A method as in claim 1, wherein the determining whether the monitored thermal emissivity levels correspond to at least one calibrated thermal emissivity level associated with the object of interest comprises:
   determining whether the monitored thermal emissivity level for a section of the zone of interest is associated with a calibrated thermal emissivity level for a factor selected from a group comprising: ambient background, an exterior surface of a human, a clothing material, a personal article, a computing device, and an explosive material.

17. A method as in claim 1, wherein the thermal emissivity levels are monitored from a fixed distance; and further comprising:
   empirically associating thermal emissivity levels at the fixed distance with one or more factors selected from a group comprising: ambient background, an exterior surface of a human, a clothing material, a personal article, a computing device, and an explosive material.

18. A method as in claim 1, further comprising processing successive image frames of an infrared photodetector to confirm detection of the object of interest.

19. A method as in claim 18, further comprising processing successive infrared photodetector image frames to confirm identification of a specific human carrying the object of interest.

20. A method as in claim 19, wherein processing successive infrared photodetector image frames to confirm identification of a specific human carrying the object of interest further comprises identifying a specific location of the object of interest with a margin of error less than a fraction of an inch.

21. A method as in claim 1, wherein determining whether the monitored thermal emissivity levels correspond to at least one calibrated thermal emissivity level associated with the object of interest is based on a differential emissivity, wherein the differential emissivity is buffered against changes in the ambient background including temperature, wind condition, humidity, hail, and snow.

22. A method as in claim 1, wherein monitoring thermal emissivity levels of human traffic within a plurality of sections of a zone of interest further comprises monitoring human traffic or at least one of an airport, a border crossing, an entrance to subways and other transportation facilities, an entrance to sensitive facilities, a public function, and a sporting event.

23. A method comprising:
   creating a virtual portal representing a zone of interest;
   monitoring thermal emissivity levels of human traffic within a plurality of sections of the zone of interest using an infrared photodetector;
   determining whether the monitored thermal emissivity levels correspond to at least one calibrated thermal emissivity level associated with a synthetic material concealed on a human body by:
      identifying a human associated with thermal emissivity levels corresponding to the synthetic material;
      uploading a plurality of pre-determined empirical models to compare the monitored emissivity levels against the models;
      performing model switching to compensate for a change in distance between the human and a emissivity monitoring system as the human carrying the synthetic material moves; and
      tracking the identified human within the zone of interest by comparing the detected emissivity level against the plurality of pre-determined empirical models; and
   initiating notification to a user indicating that the synthetic material is within the zone of interest.

24. An apparatus comprising:
   a radiation detection unit operable to monitor thermal emissivity levels of human traffic within a plurality of sections of a zone of interest; and
   a processor coupled to the radiation detection unit operable to determine whether the monitored thermal emissivity levels correspond to at least one calibrated thermal emissivity level associated with an object of interest by:
      identifying a human associated with thermal emissivity levels corresponding to the object of interest;
      uploading a plurality of pre-determined empirical models to compare the monitored emissivity levels against the models;
      performing model switching to compensate for a change in distance between the human and a emissivity monitoring system as the human carrying the object of interest moves; and
      tracking the identified human within the zone of interest by comparing the detected emissivity level against the plurality of pre-determined empirical models; and
      initiating notification of a user indicating that the object of interest is within the zone of interest.

25. An apparatus as in claim 24, wherein the object of interest is a concealed explosive material.

26. An apparatus as in claim 24, wherein the processor is operable to identify a human associated with each thermal emissivity level associated with the object of interest.

27. An apparatus as in claim 24, further ocmprisng a display unit; and wherein the processor is operable to track the identified human within the zone of interest and display the tracked identified human on the display.

28. An apparatus as in claim 24, wherein the radiation detection unit is operable to distinguish temperature differences within a range of about five milliKelvin to fifty milliKelvin to identify the object of interest.

29. An apparatus as in claim 24, wherein the radiation detection unit is a long wave infrared detector.

30. An apparatus as in claim 24, wherein the long wave infrared detector is a quantum well infrared photodetector.

31. An apparatus as in claim 30, wherein the plurality of sections of the zone of interest correspond to pixels of the quantum well infrared photodetector.

32. An apparatus as in claim 30, further comprising:
   a data repository coupled to the processor operable to store data associated with calibrated thermal emissivity levels for factors selected from a grouping comprising: ambient background, an exterior surface of a human, clothing, personal articles, computing devices, and an explosive material.

33. An apparatus as in claim 32, wherein the calibrated thermal emissivity levels are determined by empirically associating the factors at a distance corresponding to a length between the radiation detection unit and the zone of interest.

34. An apparatus as in claim 30, wherein the radiation detection unit includes an optical element having a focal length corresponding to the zone of interest.

35. An apparatus as in claim 30, further comprising: a video camera positioned to monitor the zone of interest; and a video display unit operable to display the zone of interest as monitored by the video camera.

36. An apparatus as in claim 30, further comprising a secondary detection system coupled to the processor operable to confirm detection of the object of interest.

37. An apparatus as in claim 30, wherein the radiation detection unit is a portable device including a portable camera, a wireless device, and a hand-held device.

38. An apparatus as in claim 30, wherein the radiation detection unit is a fixed device mounted on a building, or a vehicle.

39. An apparatus as in claim 30, wherein the radiation detection unit is a quantum well infrared photodetector sensor disguised as a regular CCD camera.

40. An apparatus comprising:
   a quantum well infrared photodetector having sensitivity range of less than fifty milliKelvin operable to monitor thermal emissivity levels of a human traffic within a plurality of sections of a zone of interest;
   a processor coupled to the quantum well infrared photodetector operable to:
      determine whether the monitored thermal emissivity levels correspond to at least one calibrated thermal emissivity level associated with a concealed explosive material on a human body by:
      identifying a human associated with thermal emissivity levels corresponding to the explosive material;
      uploading a plurality of pre-determined empirical models to compare the monitored emissivity levels against the models;
      performing model switching to compensate for a change in distance between the human and a emissivity monitoring system as the human carrying the explosive material; and
      tracking the identified human within the zone of interest by comparing the detected emissivity level against the plurality of pre-determined empirical models; and
      initiating notification of a user indicating that the explosive material is within the zone of interest; and
   a data repository coupled to the processor operable to store data associated with calibrated thermal emissivity levels.

41. An apparatus as in claim 40, further comprising:
   means for performing differential emissivity calculations and black body algebra to determine whether the monitored thermal emissivity levels correspond to at least one calibrated thermal emissivity level associate with a concealed explosive material on a human body.

42. An apparatus as in claim 40, wherein the data repository stores data associate with calibrated thermal emissivity levels for factors selected from a group comprising: ambient background, an exterior surface of a human, clothing, personal articles, computing devices, and an explosive material.

* * * * *